United States Patent [19]

Wright

[11] 4,360,699

[45] Nov. 23, 1982

[54] PROCESS FOR PREPARING A 3-PHENOXYTOLUENE AND DIPHENYL ETHER

[75] Inventor: William E. Wright, Farmington Hills, Mich.

[73] Assignee: Ethyl Corporation, Richmond, Va.

[21] Appl. No.: 333,708

[22] Filed: Dec. 23, 1981

Related U.S. Application Data

[63] Continuation of Ser. No. 104,132, Dec. 17, 1979, abandoned.

[51] Int. Cl.$^3$ .............................................. C07C 41/09
[52] U.S. Cl. .................................... 568/635; 568/632; 568/639; 568/636; 568/585
[58] Field of Search ......................................... 568/635

[56] References Cited

U.S. PATENT DOCUMENTS 1,873,537  8/1932  Brown et al. ...................... 568/635

OTHER PUBLICATIONS

Murat, Parfumerie Moderne, (1922), vol. 15, No. 3, p. 51.

Nesmeyanov et al., Methods of Elemento-Organic Chemistry, vol. (1), (1967), p. 456.

*Primary Examiner*—Bernard Helfin
*Attorney, Agent, or Firm*—Donald L. Johnson; Joseph D. Odenweller; John F. Hunt

[57] ABSTRACT

Diaryl ethers such as 3-phenoxytoluene are made by heating an aromatic hydroxy compound or mixture of such compounds with aluminum or an aluminum phenoxide forming compound such as aluminum trialkyl.

2 Claims, No Drawings

PROCESS FOR PREPARING A 3-PHENOXYTOLUENE AND DIPHENYL ETHER

This application if a continuation of application Ser. No. 104,132, filed Dec. 17, 1979, and now abandoned.

BACKGROUND OF THE INVENTION

Diaryl ethers are useful chemical compounds. For example, diphenyl ether is used as a heat transfer fluid. Likewise, 3-phenoxytoluene is an intermediate in the manufacture of several pyrethrum-type insecticides. Such diaryl ethers have been made by the Ullman reaction. This involves the reaction of a potassium salt of a phenol with a bromo or chlorobenzene in the presence of a copper catalyst.

Another method is Sendersen's reaction in which a phenol or phenol mixture is passed in the vapor phase at about 450° C. over a thorium oxide catalyst.

SUMMARY

According to the present invention a new process for making diaryl ethers is provided. In this process an aromatic hydroxy compound or mixture of such compounds is reacted with aluminum metal or an aluminum compound which will react the aromatic hydroxy compound to form an aluminum phenoxide and the resultant aluminum phenoxy mixture is heated at about 200°–500° C. Following this, the diaryl ether products are separated and recovered by known methods.

DESCRIPTION OF THE PREFERRED EMBODIMENTS

A preferred embodiment of the invention is a process for making a diaryl ether, said process comprising heating an aromatic hydroxy compound or mixture of such compounds with an aluminum phenoxide forming compound at a temperature of 200°–500° C.

The process is applicable to a broad range of aromatic hydroxy compounds. All that is required is that the aromatic hydroxy compound contains a hydroxyl group bonded to a benzene ring which is capable of reacting to form an aluminum phenoxide bond and does not contain substituents that would react with aluminum to adversely affect the process. Examples of suitable aromatic hydroxy compounds are phenol, o-cresol, m-cresol, p-cresol, p-chlorophenol, p-ethylphenol, 2,4-dimethylphenol, 4-methoxyphenol, 2-chloro-4-trifluoromethylphenol, 3-methyl-4-nitrophenol, 2,4-dichlorophenol, α-naphthyl, β-naphthyl, 4-(α-methylbenzyl)phenol, 2,6-dimethylphenol, 2-cyclohexylphenol and the like including mixtures of such aromatic hydroxy compounds.

More preferred aromatic hydroxy compounds are the mononuclear compounds including those substituted with alkyl, chloro, bromo, fluoro, haloalkyl, alkoxy, nitro and similar groups.

When a single aromatic hydroxy is used there will be only one diaryl ether formed. For example, the compound phenol will form the compound diphenyl ether and the compound m-cresol will form the compound di-(3-methylphenyl)ether. When a mixture of different aromatic hydroxy compounds is used the product will be a mixture of different diphenyl ethers. The mixture will generally include all of the possible combinations. For example, a mixture of m- and p-cresol will form a mixture containing di-(3-methylphenyl)ether, di-(4-methylphenyl)ether and 4-(3-methylphenoxy)toluene.

The proportion of each different diphenyl ether is not always what would be predicted statistically. For example, when an equal mole mixture of phenol and m-cresol is reacted the expected product mixture would contain one mole part diphenyl ether, one mole part di-(3-methylphenyl)ether and 2 mole parts 3-phenoxytoluene. Surprisingly, the proportion of diphenyl ether and 3-phenoxytoluene is much higher than would be expected and very little di-(3-methylphenyl)ether is formed. This is extremely beneficial because both major products are very useful industrial chemicals. Diphenyl ether is used as a heat transfer fluid and 3-phenoxytoluene is an intermediate for making several pyrethrum-type insecticides.

Accordingly, a highly preferred embodiment of the invention is a process for making 3-phenoxytoluene and diphenyl ether by heating a mixture of phenol, m-cresol and aluminum or an aluminum phenoxy forming compound at a temperature of about 200°–500° C., more preferably 300°–400° C. The aluminum or aluminum phenoxy forming compound reacts initially with the phenolic hydroxyl group to form a mixture of various aluminum phenoxide compounds which then react to form the various diphenyl ethers and alumina.

The process is carried out by forming a mixture of the aromatic hydroxy compound(s) with aluminum metal or an aluminum compound that will react with the aromatic hydroxy group to form an aluminum phenoxy bond. Examples of such compounds are the aluminum alkyls such as triethyl aluminum, tri-n-propyl aluminum, triisobutyl aluminum and the corresponding dialkyl aluminum hydrides and the like.

Likewise, aluminum hydride, sodium aluminum hydride, potassium aluminum hydride and the like can probably be used with good results.

The amount of aluminum or aluminum phenoxy producing compounds is more than a catalytic amount. The process proceeds by forming an aluminum phenoxide compound which decomposes at elevated temperature to form the desired diphenyl ether and alumina. The following equation illustrates the process for making 3-phenoxytoluene:

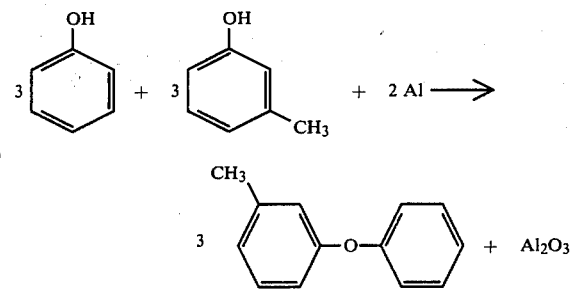

The above equation is somewhat simplified in that it does not show the aluminum phenoxide-type intermediate and shows only the production of 3-phenoxytoluene. In practice, a substantial amount of diphenyl ether will form together with a small amount of di-(3-methylphenyl)ether.

From the above stoichiometry it can be seen that up to one gram atom of aluminum can be used for each three gram moles of aromatic hydroxy compound. Lesser amounts of aluminum can be used in which case unreacted hydroxy compounds will remain in the reaction mixture for recovery and recycle. A preferred ratio is 0.1–0.2 gram atom of aluminum or gram mole of aluminum phenoxide producing compound for each 1.6–4 gram moles of aromatic hydroxy compounds. A more preferred ratio is about 0.1–0.2 gram atom of aluminum per gram mole of aromatic hydroxy compound. More aluminum can be used, but byproduct alumina tends to thicken the reaction mixture and makes it difficult to stir. An inert solvent can be used to avoid such thickening.

Temperatures from about 200°–500° C. can be used. Reaction rate increases with temperature. A more preferred temperature range is about 300°–400° C. Most reactions have been successfully conducted at about 350° C.

The reaction can be conducted without using a solvent. This is done by using less than the stoichiometric amount of aluminum. The unreacted aromatic hydroxy compound then functions as a solvent. Alternatively, an inert hydrocarbon solvent can be used. An autoclave is preferably used to prevent loss of reactants and solvent at the high reaction temperatures.

When reacting phenol and m-cresol to make 3-phenoxytoluene, a useful mole ratio of phenol to m-cresol is about 1–3:1. Best results were obtained at about 3:1 mole ratio. At this ratio with 0.1 gram atom of aluminum the product weight ratio was 30% diphenyl ether, 63% 3-phenoxytoluene and only 7% di-(3-methylphenyl)ether.

From the above discussion it can be seen that the novel feature of the process comprises heating an aluminum phenoxide or mixture of aluminum phenoxides at a temperature of about 200°–500° C., more preferably 300°–400° C., and recovering a diaryl ether from the resultant reaction mixture.

The following example serves to illustrate the manner of conducting the reaction.

EXAMPLE

In an autoclave was placed 141 grams (1.5 moles) of phenol, 54.1 grams (0.5 mole) of m-cresol and 5.4 grams (0.2 gram atom) of aluminum powder. The autoclave was sealed and flushed with nitrogen. It was then heated to 300° C. at which temperature a vigorous exothermic reaction occurred raising the temperature to 350° C. This was the reaction of aluminum with the phenolic hydroxy group to form aluminum phenoxy intermediate. The reaction mixture was cooled to 45° C. and vented. The autoclave was resealed and heated to 350° C. and stirred at that temperature for 2.3 hours. It was then cooled to room temperature and the reaction product was removed with the aid of a toluene solvent. It was washed with 33% sulfuric acid to remove alumina. Phase separation was slow. Toluene was evaporated from the organic phase under vacuum. The organic phase analyzed.

| | |
|---|---|
| phenol | 47.0 wt % |
| m-cresol | 11.0 wt % |
| diphenyl ether | 13.3 wt % |
| 3-phenoxytoluene | 19.0 wt % |
| di-(3-methylphenyl)ether | 4.7 wt % |

A series of reactions was carried out following the above general procedure. The following table gives the results:

| Reactants (moles) | | | Temp | Mole Ratio of Products[1] | | |
|---|---|---|---|---|---|---|
| Al | Phenol | m-Cresol | °C. | DPE | 3-PT | DTE |
| 0.2 | 0.6 | 1.6 | 350 | 1 | 39 | 60 |
| 0.2 | 1.0 | 1.0 | 350 | 7 | 52 | 41 |
| 0.2 | 1.5 | 0.5 | 350 | 28 | 63 | 9 |
| 0.4 | 1.5 | 0.5 | 350 | 56 | 51 | 13 |
| 0.1 | 0.5 | 0.5 | 375[2] | 9 | 47 | 44 |
| 0.4 | 1.5 | 0.5 | 350 | 33 | 53 | 14 |
| 0.4 | 1.5 | 0.5 | 300[3] | 35 | 52 | 13 |

[1] Excluding unreacted starting material "DPE" is diphenyl ether, "3-Pt" is 3-phenoxytoluene, and "DTE" is ditolyl ether.
[2] Substantial decomposition occurred.
[3] At 5 hours conversion to product based on Al was 42%.

The various products from the above example can be readily recovered by distillation.

I claim:

1. A process for making a major portion of 3-phenoxytoluene and a minor portion of diphenyl ether, said process comprising heating a mixture of about 1 to 3 mole parts phenol, 1 mole part m-cresol and 0.1 or more gram-atom parts aluminum or mole parts aluminum phenoxide forming compound in an autoclave at a temperature of about 300°–375° C.

2. A process of claim 1 wherein said aluminum phenoxide forming compound is an aluminum alkyl.

* * * * *

UNITED STATES PATENT AND TRADEMARK OFFICE
CERTIFICATE OF CORRECTION

PATENT NO. : 4,360,699
DATED : November 23, 1982
INVENTOR(S) : William E. Wright It is certified that error appears in the above-identified patent and that said Letters Patent are hereby corrected as shown below:

Column 1, line 17 - "Sendersen's" should be -- Senderens' --

In the table at Column 4, line 27, under "DPE" - 56 should be -- 36 --

Signed and Sealed this

First Day of February 1983

[SEAL]

Attest:

GERALD J. MOSSINGHOFF

Attesting Officer     Commissioner of Patents and Trademarks